(12) United States Patent
Kesper et al.

(10) Patent No.: US 7,829,344 B2
(45) Date of Patent: Nov. 9, 2010

(54) METHOD AND DEVICE FOR THE DETECTION OF HYDROGEN

(75) Inventors: Heinrich Kesper, Willingen (DE); Eduardo Cattaneo, Brilon (DE); Bernhard Riegel, Brilon (DE)

(73) Assignee: Hoppecke Batterien GmbH & Co. KG (DE)

( * ) Notice: Subject to any disclaimer, the term of this patent is extended or adjusted under 35 U.S.C. 154(b) by 91 days.

(21) Appl. No.: 12/154,516

(22) Filed: May 23, 2008

(65) Prior Publication Data

US 2009/0017551 A1    Jan. 15, 2009

(30) Foreign Application Priority Data

Jul. 12, 2007    (EP)    ................... 07013639

(51) Int. Cl.
*G01N 33/22*    (2006.01)
*G01N 33/00*    (2006.01)

(52) U.S. Cl. ............ 436/144; 422/95; 422/94; 422/83; 422/50

(58) Field of Classification Search ........ 436/144; 422/95, 94, 83, 50
See application file for complete search history.

(56) References Cited

U.S. PATENT DOCUMENTS 5,483,228 A    1/1996    Bailey et al.
6,254,841 B1 *    7/2001    Kesper et al. ............. 422/211
2003/0056570 A1    3/2003    Shin et al.

FOREIGN PATENT DOCUMENTS

| DE | 3151084 | 4/1983 |
|----|---------|--------|
| DE | 3503018 | 7/1986 |
| DE | 19645694 | 5/1998 |
| EP | 1780826 | 5/2007 |
| GB | 761055 | 11/1956 |

OTHER PUBLICATIONS

Shin, Woosuck et al., "Hydrogen-Selective Thermoelectric Gas Sensor", Synergy Materials Research Center, Sensors and Actuators (2003), pp. 304-308.

* cited by examiner

*Primary Examiner*—Walter D Griffin
*Assistant Examiner*—Christine T Mui
(74) *Attorney, Agent, or Firm*—Harness, Dickey & Pierce, P.L.C.

(57) ABSTRACT

The present invention relates to a device and a method for the detection of hydrogen in a gas volume by means of an exothermal catalytic recombination of hydrogen and oxygen present in the gas volume into water. The amount of energy that is released during such an exothermal catalytic recombination is measured in the form of a temperature difference and is compared with a stored limit value. When a corresponding limit value is exceeded an appropriate signal is output.

19 Claims, 2 Drawing Sheets

METHOD AND DEVICE FOR THE DETECTION OF HYDROGEN

BACKGROUND OF THE INVENTION

1. Technical Field

The present invention relates to a device and a method for the detection of hydrogen in a gas volume.

2. Discussion

Today, hydrogen is commercially used as an energy source in a broad field of applications. It is known for instance to operate fuel cells with hydrogen. It is also known to operate combustion engines with hydrogen. But hydrogen involves a risk of ignitable air/hydrogen mixtures being formed in the case of possible leakages of hydrogen-carrying passages or systems. The explosive limit for air/hydrogen mixtures ranges from 4 to 75% by volume. Such ignitable or explosive air/hydrogen mixtures are also named oxyhydrogen gas.

Hydrogen is a colourless, odourless and flavourless gas, which fact makes it difficult or even impossible to perceive hydrogen by human senses.

Regarding the calorific value of pure hydrogen of 13 $MJ/m^3$, leakages in hydrogen-carrying systems constitute an immense risk potential in the operation of hydrogen plants.

Hydrogen is also produced in energy stores like accumulators, especially during the charging operation. Explosive air/hydrogen mixtures may be generated in this case, too.

For the safe operation of hydrogen plants or energy stores like accumulators it is therefore necessary to securely determine the formation of ignitable air/hydrogen mixtures, in order to be able to initiate appropriate counter measures such as venting the room or interrupting the hydrogen supply.

Up to present, hydrogen is detected in prior art by means of electrochemical sensors having a two- or three-electrode device (working electrode, reference electrode and counter electrode) (example: U.S. Pat. No. 7,060,169). The sensors include a hydrogen-permeable diaphragm and are used for measurements within a concentration range lower than 5% by volume. A disadvantage of electrochemical sensors is the sensitivity which decreases over the time (aging effect). This effect is caused by the degradation of the electrolyte as well as by side reactions on the electrodes. A shortening of the service time must be expected also in the case of an over-saturation of the electrolyte when the hydrogen concentrations are very high. In the presence of high water steam concentrations corrosion on the electronics and/or the blocking of the diaphragm accompanied by a clear deceleration of the response time may occur due to the formation of condensate.

A further principle for hydrogen detection makes use of a metal thin-film (e.g. Pd), where the measuring principle is based on a change of conductivity (EP 768528) or a change of light transmission (EP 1521080) of this metal thin-film due to the incorporation of hydrogen. These methods also display a reduction of the sensitivity in case of a water condensate formation as well as through carbon monoxide absorption. With hydrogen-containing gases like $NH_3$ and $H_2S$ a reduction of the sensing capability occurs through a reduction of the selectivity of the sensor.

A further established method for measuring hydrogen in a broad concentration range is supported on the clearly lower conductivity of hydrogen compared to other gases. A drawback of this method however is the low selectivity resulting in faulty results in cases where hydrogen-containing gases are detected which include further gas components.

SUMMARY OF THE INVENTION

It is therefore a problem of the present invention to provide a device for the detection of hydrogen in a gas volume as well as a corresponding method for the detection of hydrogen.

Concerning the device, this problem is solved by a device for the detection of hydrogen in a gas volume, comprising a device for the exothermal catalytic recombination of hydrogen in the presence of oxygen into water, a device for the determination of the temperature change during the recombination, a device for comparing the temperature change that occurred during the recombination with a stored limit value, and a device for outputting a signal, wherein the device for the recombination of hydrogen is connected to the device for the determination of the temperature change occurring during the recombination in such a manner that a substantially faultless determination of the temperature change of the catalyst occurring during the recombination can be made, and wherein the device for comparing the temperature change occurring during the recombination with the stored limit value is connected to the device for outputting a signal in such a way that a signal is output when the stored limit value is exceeded.

Advantageously, the device according to the invention makes it possible both to detect hydrogen (oxyhydrogen) and to degrade the hydrogen fraction, namely to a value below the explosive limit of 4% by volume.

The operation principle of the device according to the invention is here based on the exothermal catalytic recombination of hydrogen in the presence of oxygen into water. By a temperature change occurring at the catalyst this device makes the detection of hydrogen possible. The device allows for a direct correlation between the occurring hydrogen concentration and temperature increase compared to a reference temperature (see FIG. 1).

By the catalytic recombination of the hydrogen present in the gas volume with oxygen into water there is simultaneously reduced the hydrogen concentration for measuring. With the device of the invention being correspondingly configured, it is possible in this way to reduce the hydrogen concentration in a gas volume to a value lower than the explosive limit and to avoid the risk that is radiated by hydrogen.

Concerning the method, the problem of the invention is solved by a method for the detection of hydrogen, said method including the steps of contacting a gas volume to be detected for hydrogen with a catalyst for the exothermal catalytic recombination of hydrogen in the presence of oxygen into water; determining the temperature increase on the catalyst occurring during the exothermal catalytic recombination; comparing the determined temperature difference with a stored limit value by a suitable device, wherein said device outputs a signal in case that the stored limit value is exceeded.

Preferably, the catalyst that is used in the device for the catalytic recombination of hydrogen comprises a platinum metal, especially platinum or palladium. The catalyst may be applied to a substrate.

In a preferred embodiment of the device for the catalytic recombination of hydrogen the catalyst is tempered or applied to a tempered substrate, in order to avoid condensation.

Advantageously, the catalyst including a platinum metal is coated with a porous metal material (see FIG. 2). Advantageously, said porous material is a ceramic material or a glass frit material.

In an advantageous construction of the device for the detection the porous material itself is coated in turn with an absorption material. Here the absorption material serves the absorption of inhibitors that may negatively influence the reactive surface of the catalyst as a catalyst poison. Correspondingly suitable absorption materials are for instance silver oxide, iron oxide, copper oxide or manganese oxide as well as mixtures of these oxides.

For the determination of the temperature difference occurring during the recombination devices are suitable such as thermometers, temperature sensors or thermal elements.

The device for the comparison of the temperature difference occurring during the recombination with a stored limit value can advantageously be a comparator circuit or computer unit.

The construction in the form that the catalyst material of the device for the catalytic recombination is coated with a porous material like for instance a ceramic material or a glass frit material that is coated in turn with an absorption material of the aforementioned kind guarantees that in the case of a humidity absorption by the hydrophobed absorption material the catalyst is not negatively influenced concerning its catalytic effect. In addition, as described above, the gases advancing to the catalytic surface of the device for the recombination of hydrogen are purified in the fashion of a filter, thus removing disturbing substances like for instance hydrides or sulphur compounds. Hydrides or sulphur compounds are able in their quality as a catalyst poison to reduce the activity of the platinum metals used as a catalyst and thus negatively influence the performance of the detection device.

The gas that is to be detected and that possibly contains hydrogen and additionally includes oxygen, for instance in the form of atmospheric oxygen, can be led to the catalyst surface of the device for the catalytic recombination through the absorption material and the porous material by suitable installations for conveying and transporting gases such as pumps or fans. Alternatively, the gas may be allowed to advance to the catalytic surface merely by diffusion.

On the catalyst surface itself the hydrogen which is possibly present in the gas volume to be detected is catalytically recombined into water in the presence of oxygen. This recombination is a strongly exothermal reaction in which energy of about 280 kJ/mol hydrogen is released.

This energy is released in the form of thermal energy. This leads to a temperature change on the catalyst surface of the device for the recombination. The water that is produced during the recombination can be removed in the form of water steam.

It turned out that due to the enormous amount of energy that is released during the catalytic recombination of hydrogen this energy release is suitable as a sensitive probe for the detection of hydrogen in gas volumes.

According to the present invention, the amount of energy released by the catalytic recombination is determined by measuring a relative temperature change $\Delta T$ on the catalyst surface. By measuring a relative temperature difference the device of the invention as well as the method of the invention are advantageously almost uninfluenced by the ambient temperature.

The relative temperature change determined during the catalytic recombination can be compared with a stored limit value in a comparator circuit or a computer unit. Here the limit value of the temperature change corresponds to a temperature change as the same is provoked by a hydrogen concentration on the device for the catalytic recombination which is to be defined as a limit.

Devices which are available today for the determination of temperatures comprise temperature sensors like digital (electronic) thermometers, resistance thermometers, IR sensors or thermal elements having a very high precision. In addition to that, they are insensitive to corrosion and other aggressive influences.

If the device for the comparison of the temperature change occurring during the recombination with the stored limit value determines that the temperature difference limit has been exceeded, the same can output a corresponding signal through an outputting device. This signal may be a control signal for controlling an optical and/or acoustic signalling device that is suitable in the form of a warning light or a warning siren to inform persons about a corresponding hydrogen concentration as the same corresponds to the stored limit value.

In addition to that, by means of said control signal output by the outputting device a corresponding event following the exceedance of the hydrogen limit value can be triggered such as for instance the closing of valves in hydrogen-carrying passages, in order to interrupt the hydrogen supply to installations, or the starting of corresponding ventilation systems for the ventilation of installations or systems, in order to reduce the hydrogen concentration present in these installations or systems to a value below a corresponding limit value. It is of course within the scope of the present invention to control other installations in dependence of the detected hydrogen with the aid of the control signal output by the outputting device.

In a preferred embodiment of the device according to the invention the same includes a heating installation for tempering the device for the catalytic recombination of the hydrogen. Thereby the deposition of condensate humidity in the device can be avoided and its operational readiness for the detection of hydrogen guaranteed over a broad range of operating conditions.

In a further preferred embodiment the device for the catalytic recombination and the device for the comparison of the temperature change occurring during the recombination with a stored limit value are spatially delimited one against the other that any introduction of hydrogen to the device for the comparison, which may be a comparator circuit or a computer unit, is avoided to prevent possible ignition reactions of the hydrogen by electric sparks.

The device of the invention for the detection of hydrogen can be manufactured as a complex device in view of the miniaturization of electronic circuits that is possible today, so that the device will require only little space. Due to this fact the device of the invention can advantageously be incorporated in corresponding hydrogen-operated or hydrogen-carrying systems like fuel cells, hydrogen compressors, hydrogen fuel stations, hydrogen-operated vehicles and the like. The coupling of the device of the invention to the control devices of the above-described systems accordingly leads to a clearly improved operation safety of the systems.

Moreover, the device of the invention can be used also for the manual detection of leakages in passage systems or installations by having a corresponding detecting unit incorporated in the device. This detection unit may be a pump for sucking in gas volumes via a corresponding probe, wherein the pump supplies the sucked-in gas volume to a device according to the invention for detection. When a corresponding limit value of a hydrogen concentration is exceeded, a suitable signal can be output. Here the limit concentration can be correspondingly varied by a variation of the limit value for the temperature change. Finally, also a correlation between the temperature on the catalyst surface and a current hydrogen concentration is possible, so that the device of the invention can also serve for incorporation in a system for measuring the hydrogen concentration in a gas volume.

Due to the possibility of configuring devices according to the invention with a complex structure, it is also provided according to the invention to interlink several devices of the invention, in order to be able to monitor also larger hydrogen-carrying systems or installations for possible leakages (FIGS. 3 and 4).

DESCRIPTION OF THE PREFERRED EMBODIMENTS

Figure 1:
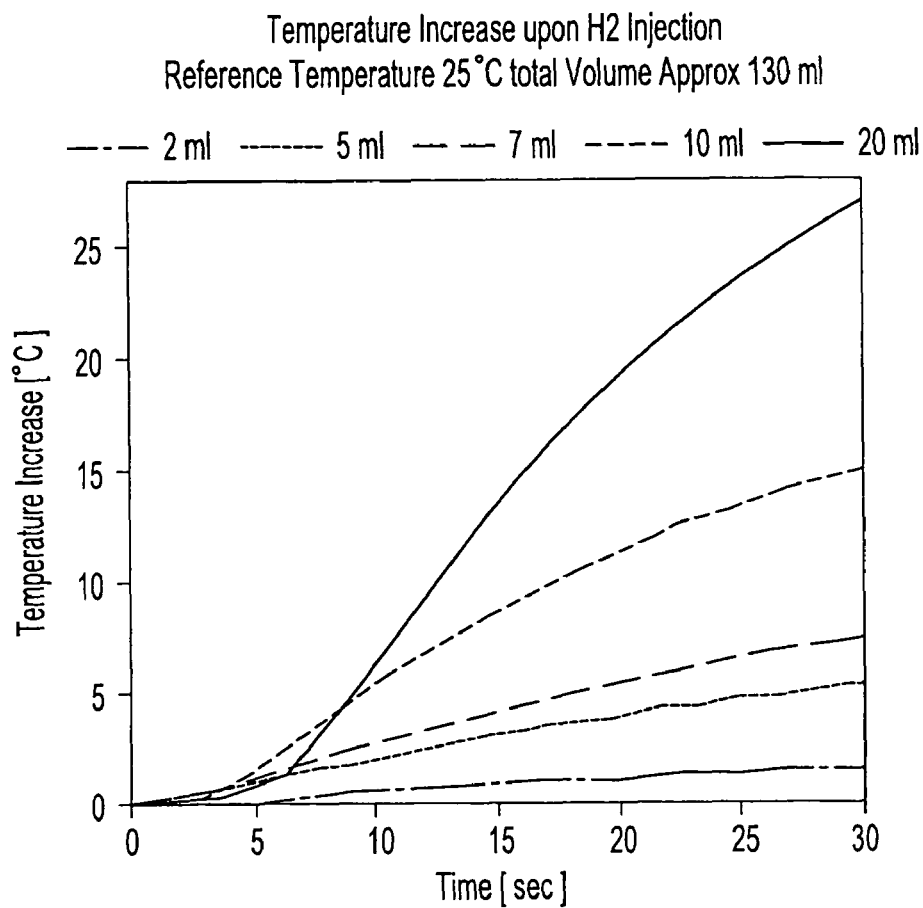
FIG. 1 shows a diagram relating to a temperature increase of the catalyst as a function of time, in dependence of the $H_2$ concentration.

FIG. 1 shows the temperature curve on a catalyst surface for the catalyst reformation of hydrogen and oxygen into water. In dependence of the hydrogen concentration in the gas volume to be examined a temperature increase on the surface of the catalyst is observed. In the present case the temperature curve of a platinum metal surface at the exposition of a hydrogen concentration of about 1.5% by volume, 3.9% by volume, 5.4% by volume, 7.8% by volume and 15.4% by volume, respectively was monitored. The underlying basis temperature was about 25° C. A gas volume of approx 130 ml was respectively charged with 2 ml, 5 ml, 7 ml, 10 ml or 20 ml $H_2$. After 30 seconds a temperature increase of approx 1.5° C., 5° C., 7.5° C., 15° C. respectively 27° C. was observed. If, according to the invention, a limit value of 1.5° C. is stored and if this limit value is exceeded on the catalyst surface within one measuring cycle of e.g. 30 seconds, there is a $H_2$ concentration of >2% by volume. Accordingly, a safe determination of the hydrogen concentration in gas volumes which is also largely insensitive to external influences is possible. In an advantageous manner the device of the invention also leads to a reduction of the hydrogen concentration in gas volumes by the exothermal recombination reaction to a level below the explosive limit.

Figure 2:
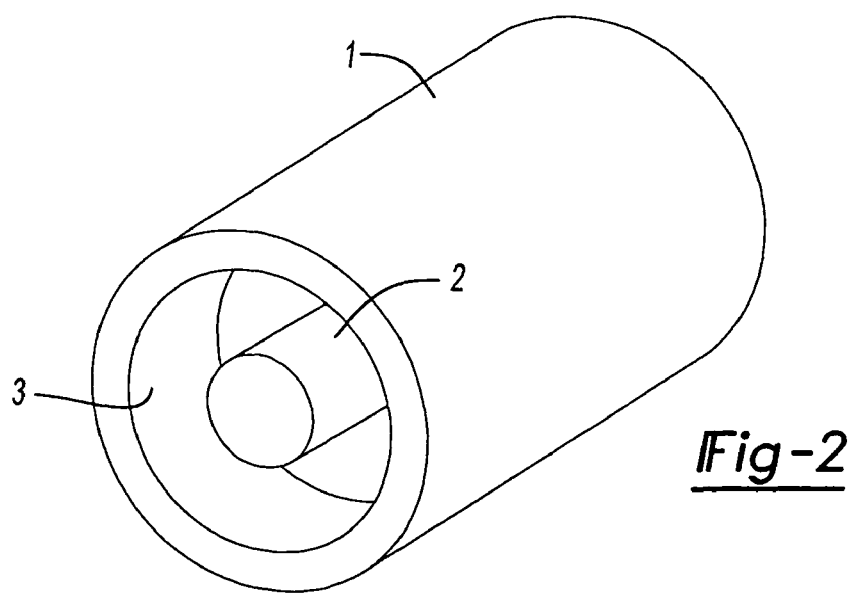
FIG. 2 shows the structure of a detection device according to the invention.

FIG. 2 shows the structure of a detection device according to the invention. Here reference number 1 designates a porous ceramic coating, 2 a catalyst pin and 3 an absorber space. The catalyst pin 1 is coated with a porous ceramic material 2, which material is to protect the catalyst surface against disturbing influences. Between the catalyst pin 1 and the absorber material an absorber space 3 is formed into which the gas mixture can penetrate through the absorber material 2 and react there on the surface of the catalyst pin 1.

Figure 3:
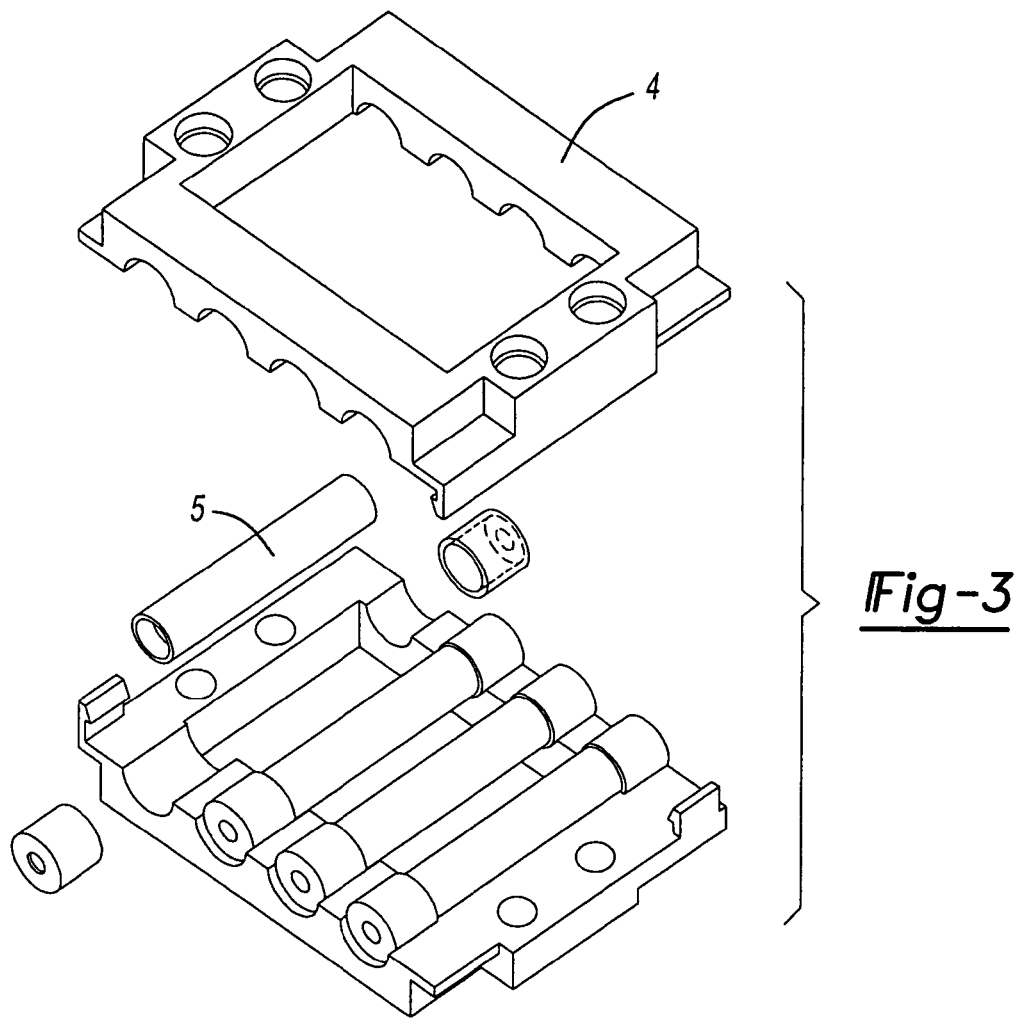
FIG. 3 shows the structure of an interlinked device unit.
Figure 4:
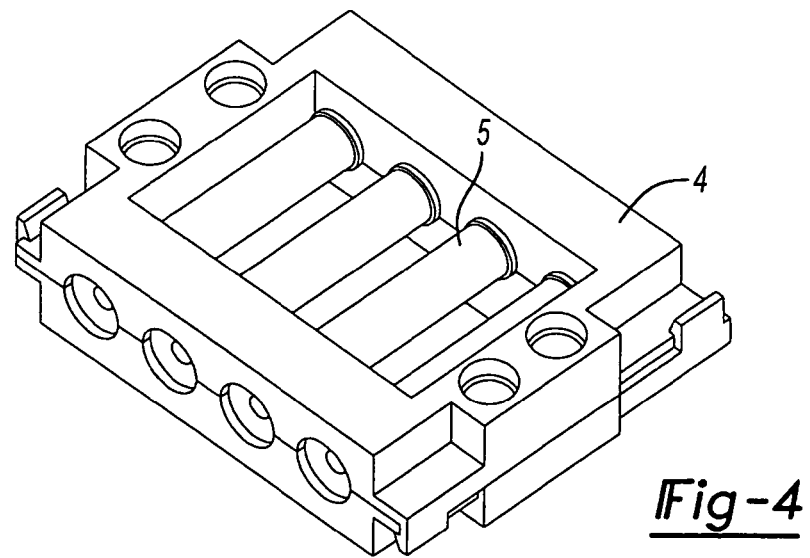
FIG. 4 shows an interlinked device unit.

The FIGS. 3 and 4 show an interlinked device according to the invention for the detection of hydrogen, in which device several detection elements 5 that respectively consist of a catalyst pin 1, a ceramic material 2 and an absorber space 3 are received in a common seat 4. The recombination volume of the interlinked unit is thereby increased and the degradation of the hydrogen concentration through the catalytic recombination takes place more rapidly. This contributes in turn to an increase in the operation safety of hydrogen plants.

What is claimed is:

1. A device for detection of hydrogen in a gas volume, the device comprising:
    a device for exothermal catalytic recombination of hydrogen in the presence of oxygen into water; the device having a catalyst that is surrounded by a porous material, wherein the porous material is adapted to allow passing of a gas of the gas volume therethrough;
    a device for determination of a temperature change occurring during the recombination process, wherein the device for exothermal catalytic recombination of hydrogen in the presence of oxygen into water is connected with the device for determination of a temperature change occurring during the recombination process in such a manner that a substantially faultless determination of the temperature change of the catalyst surface of the device for exothermal catalytic recombination of hydrogen in the presence of oxygen into water occurring during the recombination process occurs;
    a device for comparison of a stored limit value with the temperature change that occurs during the recombination process; and
    a device for outputting a signal, wherein the device for comparison of a stored limit value with a temperature change occurring during the recombination process is connected with the device for outputting a signal in such a manner that a signal is output when the stored limit value is exceeded.

2. The device according to claim 1, wherein the catalyst is platinum or palladium.

3. The device according to claim 2, wherein the catalyst is surrounded by a coating made from the porous material.

4. The device according to claim 3, wherein the coating is covered by a coating made from an absorption material.

5. The device according to claim 3, wherein the porous material is a ceramic material or a glass frit material.

6. The device according to claim 4, wherein the absorption material includes at least one material selected from the group consisting of silver oxide, iron oxide, copper oxide, magnesium oxide, and mixtures thereof.

7. The device according to claim 2, wherein the catalyst is applied to a substrate.

8. The device according to claim 7, wherein the substrate is an aluminium-silicon oxide, $Al_2O_3$ or $SiO_2$ (amorphous silicate) material.

9. The device according to claim 1, wherein the device for determination of a temperature change occurring during the recombination process is a thermometer, a temperature sensor, or a thermal element.

10. The device according to claim 1, wherein the device for comparison of a stored limit value with the temperature change occurring during the recombination process is a comparator circuit or a computer unit.

11. The device according to claim 1, further comprising at least one of an optical and acoustic signaling device, wherein the device for outputting a signal outputs a control signal controlling the optical and acoustic signaling device.

12. The device according to claim 1, further comprising a valve or a ventilation system, wherein the device for outputting a signal outputs a control signal controlling the valve or the ventilation system.

13. A method for the detection of hydrogen in a gas volume, comprising the steps of:
    passing gas of the gas volume through a porous material surrounding a catalyst for exothermal catalytic recombining of hydrogen in the presence of oxygen into water;

contacting said catalyst with said gas to recombine hydrogen in the presence of oxygen into water such that a temperature change of the catalyst occurs;

determining a temperature difference occurring at the catalyst during the exothermal catalytic recombination process; and comparing the determined temperature difference with a stored limit value by means of a suitable device, wherein said device outputs a signal when the stored limit value is exceeded.

14. The method according to claim 13, wherein the catalyst includes platinum or palladium.

15. The method according to claim 13, wherein a thermometer, a temperature sensor, or a thermal element determines the temperature difference.

16. The method according to claim 13, wherein a comparator circuit or a computer unit compares the determined temperature difference with a stored limit value.

17. The method according to claim 13, wherein the catalyst is heated.

18. The method according to claim 13, further comprising the step of passing the gas through an absorption material.

19. A device for detecting hydrogen in a gas, the device comprising:

a recombination device comprising a pin including a catalyst and a cylindrical member that surrounds said pin, said cylindrical member being formed of a porous material and an absorption material that allows at least hydrogen and oxygen of the gas to pass therethrough such that said hydrogen and oxygen contacts said catalyst after passing through said porous material, wherein once said hydrogen and oxygen contact said catalyst, said hydrogen and oxygen undergo an exothermic recombination to form water that raises a temperature of said catalyst;

a temperature determination device connected to said recombination device that determines said temperature of said catalyst during said recombination process;

a comparison device that compares said temperature with a stored temperature value; and a signal device that outputs a signal if said temperature exceeds said stored temperature value, wherein said absorption material absorbs inhibitors from said gas that negatively influence a reactive surface of said catalyst.

* * * * *